(12) United States Patent
Ryu (10) Patent No.: US 9,366,619 B2
(45) Date of Patent: Jun. 14, 2016

(54) OPTICAL DEVICE FOR PERFORMING AN ASSAY

(75) Inventor: Gihan Ryu, New Malden (GB)

(73) Assignee: Molecular Vision Limited, London (GB)

( * ) Notice: Subject to any disclaimer, the term of this patent is extended or adjusted under 35 U.S.C. 154(b) by 0 days.

(21) Appl. No.: 14/233,627

(22) PCT Filed: Jul. 20, 2012

(86) PCT No.: PCT/GB2012/000607
§ 371 (c)(1),
(2), (4) Date: Mar. 26, 2014

(87) PCT Pub. No.: WO2013/014407
PCT Pub. Date: Jan. 31, 2013

(65) Prior Publication Data
US 2014/0219870 A1  Aug. 7, 2014

(30) Foreign Application Priority Data
Jul. 22, 2011 (GB) .................................. 1112726.3

(51) Int. Cl.
| | |
|---|---|
| *G01N 21/05* | (2006.01) |
| *B01L 3/00* | (2006.01) |
| *G01N 21/64* | (2006.01) |
| *G01N 33/543* | (2006.01) |
| *G01N 21/03* | (2006.01) |

(52) U.S. Cl.
CPC .......... *G01N 21/05* (2013.01); *B01L 3/502715* (2013.01); *G01N 21/6452* (2013.01); *G01N 33/54373* (2013.01); *B01L 2300/0654* (2013.01); *B01L 2300/0816* (2013.01);

(Continued)

(58) Field of Classification Search
CPC ............ G01N 21/05; G01N 33/54373; G01N 21/6452; G01N 2021/052; G01N 2021/0325; G01N 2021/0346; B01L 3/502715; B01L 2300/0816; B01L 2300/0654; Y10T 29/49826
See application file for complete search history.

(56) References Cited

U.S. PATENT DOCUMENTS

| | | | |
|---|---|---|---|
| 5,071,248 A | * 12/1991 | Tiefenthaler | ......... G01N 21/431 356/128 |
| 6,341,185 B1 | 1/2002 | Elster et al. | |

(Continued)

FOREIGN PATENT DOCUMENTS

| | | |
|---|---|---|
| EP | 1 942 341 | 7/2008 |
| JP | 2005221327 | 8/2005 |

(Continued)

OTHER PUBLICATIONS

Great Britain Application No. GB1112726.3 filed Jul. 22, 2011 search report dated Oct. 27, 2011.

(Continued)

*Primary Examiner* — Lore Jarrett
(74) *Attorney, Agent, or Firm* — McDonnell Boehnen Hulbert & Berghoff LLP (57) ABSTRACT

There is provided a device, such as a microfluidic device, for performing an assay including: a substrate comprising a channel, such as a microfluidic channel; at least one optical element having an input port arranged to be optically coupled to a light source; an output port optically coupled to at least a portion of the channel; and a light guide portion optically connecting the input port and output port; and a detection port optically coupled to said at least a portion of the channel. The device provides an improved geometry which addresses problems related to traditional orthogonal detection arrangements and in-line detection systems.

18 Claims, 5 Drawing Sheets

(52) U.S. Cl.
CPC ............... *G01N 2021/0325* (2013.01); *G01N 2021/0346* (2013.01); *G01N 2021/052* (2013.01); *Y10T 29/49826* (2015.01)

(56) References Cited

U.S. PATENT DOCUMENTS

| | | |
|---|---|---|
| 2002/0024662 A1 | 2/2002 | Ueno et al. |
| 2004/0246597 A1 | 12/2004 | Ono et al. |
| 2006/0068490 A1* | 3/2006 | Tang ............... B01F 5/0603 435/287.2 |
| 2008/0277606 A1* | 11/2008 | Wang et al. ............... 250/581 |
| 2009/0140170 A1 | 6/2009 | Nevill et al. |
| 2011/0157692 A1 | 6/2011 | Lin et al. |

FOREIGN PATENT DOCUMENTS

| | | |
|---|---|---|
| WO | 99/52633 | 10/1999 |
| WO | 2006/010367 | 2/2006 |
| WO | 2010/104497 | 9/2010 |
| WO | 2011/026030 | 3/2011 |

OTHER PUBLICATIONS

International Search Report dated Sep. 28, 2012 for International Application No. PCT/GB2012/000607 filed Jul. 20, 2012.

* cited by examiner

OPTICAL DEVICE FOR PERFORMING AN ASSAY

This application is a U.S. National Phase application of International Patent Application No. PCT/GB2012/000607 filed on Jul. 20, 2012, which claims the benefit of Great Britain patent application 1112726.3, filed Jul. 22, 2011.

FIELD

The present invention relates to a device for performing an assay or method of fabricating a device for an assay. In particular, the present invention relates to a microfluidic device.

BACKGROUND

There is a well established and growing need for the measurement of analytes, e.g. albumin or troponin I, which are markers for medical conditions, in samples taken from either humans or animals. At the present time the vast majority of tests carried out to measure biological compounds in a sample are carried out using laboratory based equipment. Such tests require transport of the sample to be tested to the laboratory from the place where the sample was taken from. This can cause delays in obtaining the results of the analysis, which may be disadvantageous.

Analytical systems have been developed, and commercialised that can be used at sites remote from the laboratory, thereby obviating the need for transportation of the sample and the consequential delay. Such systems normally contain a cartridge or test strip into which a small sample of a test fluid is applied, e.g. for in vitro diagnostic assays the sample may be blood, plasma, serum, urine or amniotic fluid. The cartridge also contains reagents that will selectively bind to or react with the analyte to form a target material or substance of interest such as a compound or complex or reaction mixture. In order to determine the concentration of the analyte, the cartridge is placed in a "reader" which uses optical or other means to quantify the compound or complex and thereby determine the concentration of analyte. Laboratory based analytical systems often use fluorescent measurement of dye molecules to determine the concentration of the analyte. Cartridge-reader systems can also use fluorescent measurement but have a disadvantage in that in order to achieve the desired test performance they have to use expensive, bulky optical components.

Figure 1:
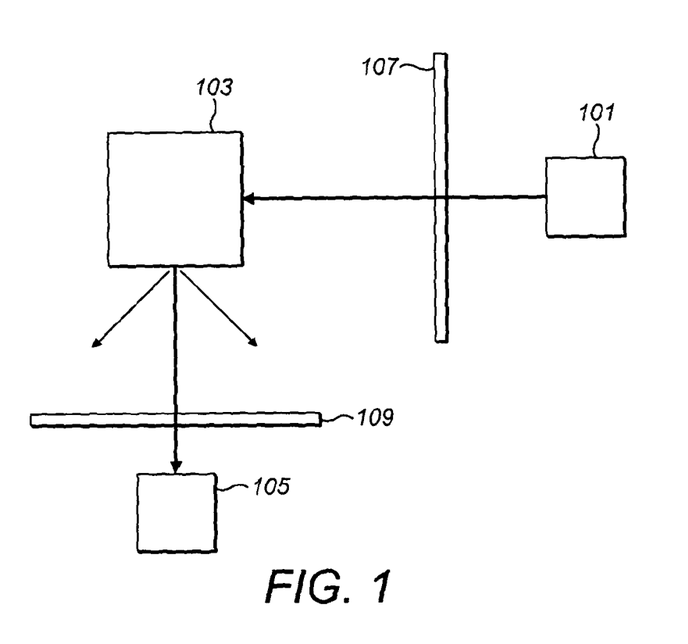
FIG. 1 shows a traditional orthogonal system for detection.

Traditionally, an optical configuration such as that shown in FIG. 1 is used for fluorescence detection in which the source 101 and detector 105 are orthogonal so that source light transmitted through the sample 103 is not directly incident upon the detector. Such devices may additionally require a short pass filter 107 and long pass filter 109. These optical probing arrangements are bulky and cumbersome to engineer into a low cost design.

Conventional fluorescent configurations of the type depicted in FIG. 1 utilise a (typically) 90° change in direction of light path between the incident source and emitted light measurement. Such arrangements are efficient but do not easily permit the light source and detector to be fabricated as a single assembly.

Alternative arrangements for optically probing a target material or substance of interest have been disclosed using in-line detection systems, that is where the light source, detection zone (containing the target material), optical detector and other required optical elements share a common optical path. Such systems have been considered for microfluidic devices.

Figure 2:
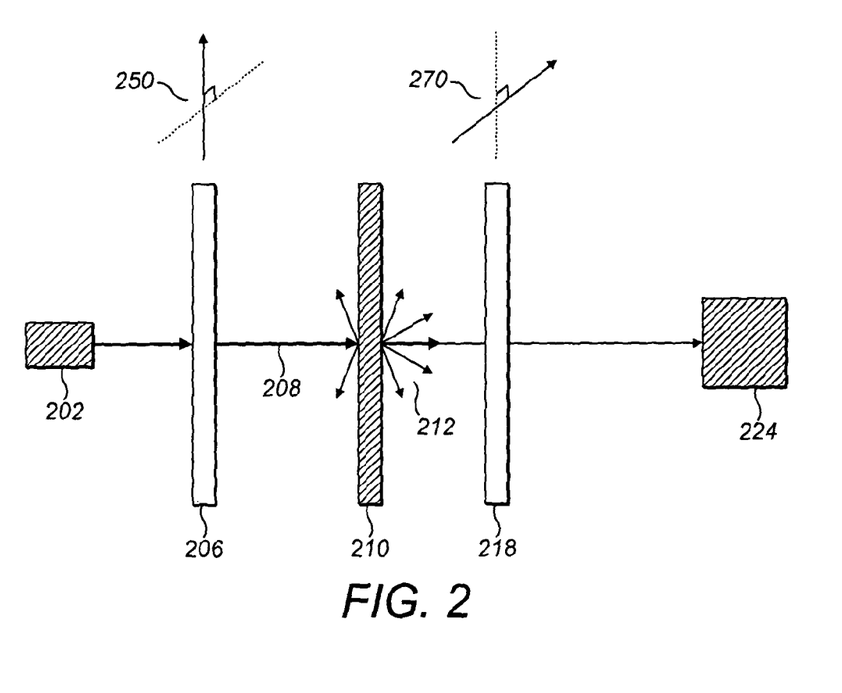
FIG. 2 shows an in-line system for detection.

An example of a known in-line detection system is shown in FIG. 2 including a light source 202, a first linear polariser 206 having a first polarisation direction 250, a target material 210, a second linear polariser 218 (having a second polarisation direction 270 orthogonal the first polarisation direction 250) and an optical detector 224. Polarised light 208 incident upon the target material 210 may give rise to the emission of unpolarised fluorescent light 212 some of which passes through the second polariser 218 to be detected by the detector 224. Stray polarised light from the source is extinguished by the second polariser owing to the orthogonal polarisation. In practice, it is found that a small proportion of incident light is transmitted through the polarisers and is detected by the detector. This leakage light can be of a magnitude such that at very low levels of emitted fluorescent light, as in the case of the analysis of very low concentration samples, it represents a significant interference and decreases the signal to noise ratio, leading to a loss of sensitivity of the test.

The present disclosure relates to an improved device for performing an assay. In particular, the present disclosure relates to a compact, low cost design which addresses problems related to orthogonal detection and in-line detection.

SUMMARY

Aspects of the invention are defined in the appended independent claims.

Accordingly, a configuration is provided in which the source and detector are arranged in an improved configuration which is not vulnerable to stray light, like the in-line system. Furthermore, the configuration is simple and can be formed using low cost materials. Further advantageously, a complex arrangement of filters and/or polarisers is not required. In particular, the configuration is relatively easy to construct in comparison to traditional orthogonal systems. The device can be formed by simply engaging an optical device with the channel (e.g. microfluidic channel) and attaching the source and detector, perhaps as a single entity, to the same side of the substrate (e.g. microfluidic chip). This arrangement allows the light source and light detector to be mounted side-by-side on the same side of the substrate thereby further simplifying the manufacturing process.

The device in accordance with the present disclosure provides a source-detector configuration which offers advantages of further preventing any stray incident light from the source reaching the detector, and permitting a single entity construction by locating both the light source and detector on a common framework or subassembly. This is because the input optical channel of the optical element and output optical channel of the device are substantially parallel and spatially offset. The source and detector are therefore substantially parallel and mountable on the same side of the device.

The arrangement requires light input to a light guide portion in such a manner that the light intensity at the channel is sufficient to excite the fluorophores, for example, present and emit sufficient light that can be detected by the detector. The loss of light intensity from the light source is not of a magnitude to prevent sufficient light reaching the detection zone via a detection port.

Light losses through transmission, scattering and absorption might be expected to lead to only very small quantities of light being directed into the detection zone. In a further improvement, the presence of a curved reflecting surface, optionally coated with a reflective material, increases the amount of light delivered to the channel. This further helps avoid the need for additional optical components such as lenses or more intense light sources such as lasers.

In an embodiment, the light detector and light source can be mounted from the same side of the substrate. This significantly reduces manufacturing complexity and costs. For example, the source and detector could be formed as component parts of a single entity.

In an embodiment, an output port is provided which delivers light to the channel by being arranged in close proximity or directly adjacent or abutting the channel. This provides a simple and convenient means for engaging with the channel.

In an embodiment, the optical axis associated with the input port is substantially parallel to the optical axis associated with the detection port. This means that the source and detector can be easily mounted and aligned.

In another embodiment, a first surface of the optical device is shaped and/or coated to reflect light to the light guide portion so as to increase the amount of light reaching the channel and increase the sensitivity of the device.

In an embodiment, the device is monolithic or forms a single entity. For example, the device may be injection moulded. Optionally, a dye may be embedded in the mould to provide selective optical filtering. Optionally, the dye may act as a short pass filter or long pass filter. Accordingly, the device may be manufactured at low cost and may be integrally formed with the substrate. Furthermore, optical filtering may be inherently added such that additional components are not required and cost and complexity is further reduced.

In another embodiment, the channel further comprises at least one of optically transparent beads, baffles, scaffold, rod or tubing arranged to support a reagent contained with the detection zone. This acts to increase the surface area over which reagent is spread and which is exposed to the incident light within the channel and increase the amount of emission, such as fluorescence or phosphorescence, thereby increasing the sensitivity of the device. An additional benefit of such arrangement is that the deposition or immobilisation of a reagent on the surface of the beads, baffles, scaffold, rod or tubing can be performed independently of the fabrication of the device allowing separate in-process tests during manufacture to minimise scrap and permitting a homogenous covering with minimal device-to-device variation. A further advantage of this design is the minimising of dead volume within the channel, allowing the efficient flushing of excess liquid phase reagents from the channel leading to faster tests that use a smaller sample volume.

In a further embodiment, the inner surface of at least a portion of the channel forming the detection zone is arranged to directly or indirectly support a reagent, such as the capture antibody for an immunoassay, through adsorption or covalent linkage, for example. Surprisingly, it is found that this embodiment is favourable for the optical arrangement of the device. Advantageously, this approach is simple and does not require additional components such as the beads, baffles, scaffold, rod or tubing of other embodiments.

BRIEF DESCRIPTION OF DRAWINGS

Embodiments of the invention will now be described by way of example with reference to the drawings in which like reference numerals will be used for like parts. In the drawings.

DETAILED DESCRIPTION OF DRAWINGS

In overview, the present disclosure relates to a device arranged to accommodate a light source and associated detector in an improved configuration for detecting or measuring fluorescence, for example, within a sample contained in a channel. The present disclosure is equally applicable to detection or measurement of phosphorescence or turbidity, for example. Any reference to fluorescence or fluorophores throughout this document is by way of example only. The present disclosure may be particularly suitable for a microfluidic device and detection within a microfluidic channel.

A microfluidic device in which no external input (such as pumping) used to create fluid flow through the device may be referred to as a passive microfluidic device. In such devices, fluid flow is encoded by the structure and composition of the device and occurs due to capillary forces.

Sample liquid for testing, containing an unknown quantity of a material of interest, is placed in an inlet reservoir. By capillarity, for example, sample liquid is drawn into at least one channel. The sample liquid passes through the microfluidic channel into an outlet reservoir.

Optical probing may be conducted at one or more points along the channel. These points may be referred to as detection zones. Optionally, physical delay loops may be incorporated into the channel to allow for certain reactions and processes to occur before and/or after optical probing. An example of a delay loop is an additional length of channel.

Figure 3:
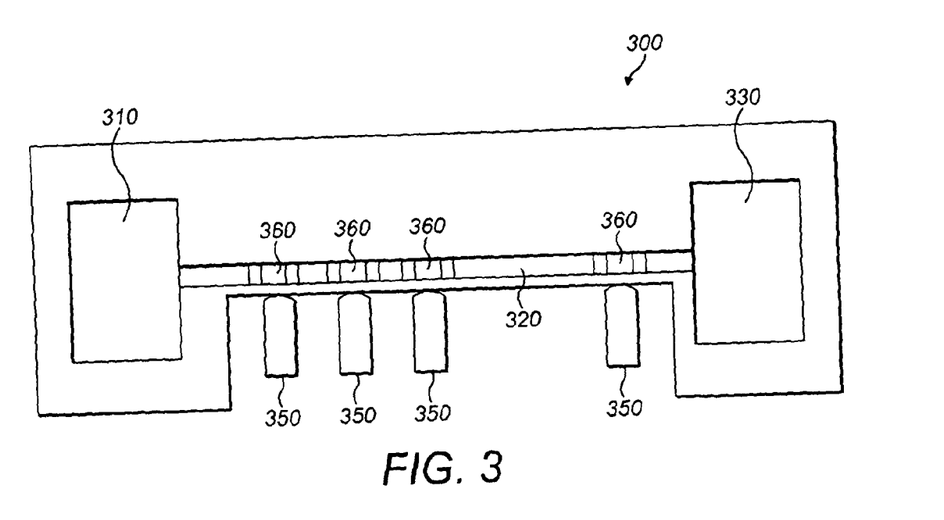
FIGS. 3, 4a and 4b show devices in accordance with the present disclosure.
Figure 4A:
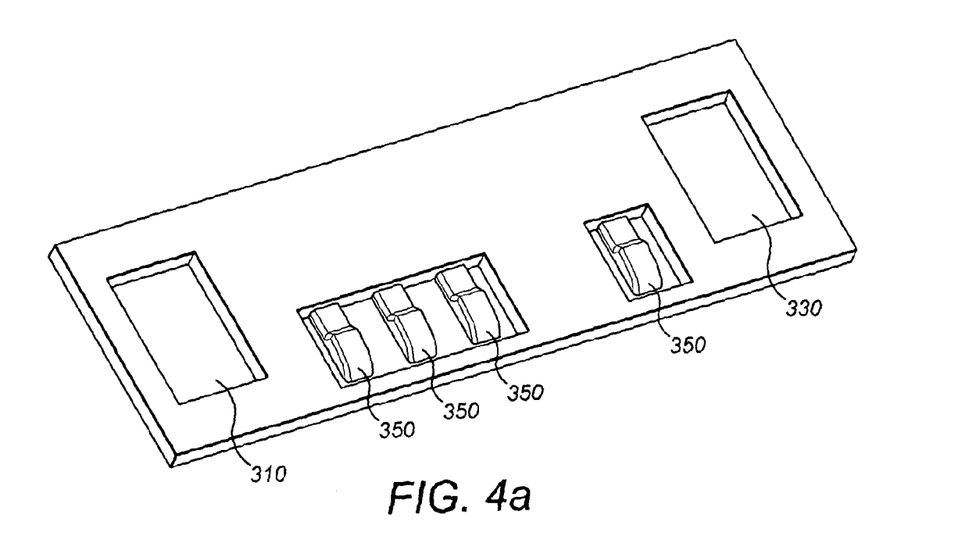
Figure 4B:
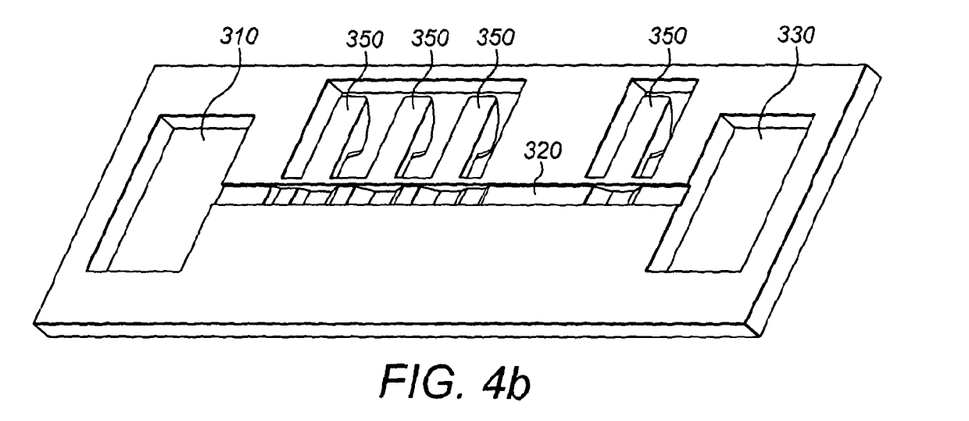

FIGS. 3, 4a and 4b show an embodiment of the present invention comprising a microfluidic device 300 having an inlet reservoir 330, a microfluidic channel 320 and an outlet reservoir 310. FIG. 3 also shows four optical elements 350 in accordance with the present disclosure. The skilled person will understand that any number of optical elements may be used providing, of course, that there is enough physical space. Each of the optical elements may be uniquely associated with a light source and corresponding detector and define a detection zone 360 within the microfluidic channel 320. One of the optical elements may be used for reference measurements such as background light measurements.

In the device illustrated in FIG. 3, the channel 320 is 49 mm long, 2 mm wide and 0.2 mm deep. In the four detection zones 360 (3 mm long, 2 mm wide) the depth increases to 1 mm.

Figure 5:
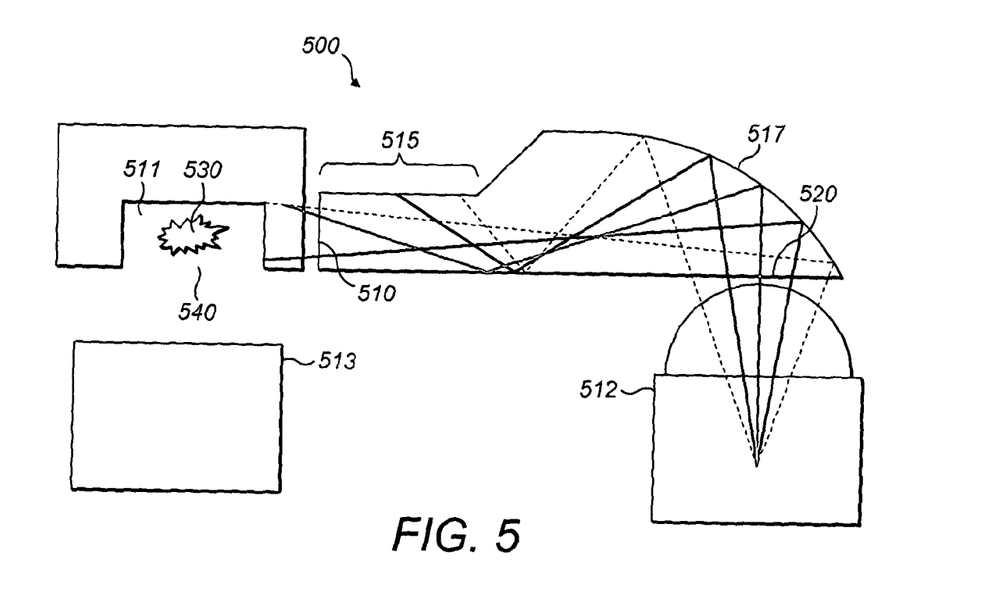
FIGS. 5 and 6 show the input light path in accordance with embodiments of the invention.

FIG. 5 shows the device arranged to allow for optical probing such as fluorescence measurement. The device is arranged to engage with a light source 512 and light detector 513 in an improved geometry which addresses problems related to traditional orthogonal detection arrangements and low cost in-line detection systems.

The optical element 500 comprises a substantially planar rectangular base. The upper surface of the element (the surface opposite the base) comprises a curved portion (surface 517) extending longitudinally from a proximal edge of the base to provide a domed ceiling over approximately one half of the base. The upper surface then tapers down to a form a planar ceiling (substantially parallel with the base) over the remaining portion of the base. The planar ceiling terminates at a wall extending perpendicularly from the distal edge of the base. This wall comprises an output port 510 which is therefore also perpendicular to the base. The side walls of the optical element 500 are perpendicular to the ceiling and base, and adjoin the two. The portion of base under the domed ceiling comprises an input port 520 adjacent to the proximal edge. The part of the device having the planar ceiling forms a light guide portion 515.

The output port 510 at the end of the light guide portion 515 engages with a microfluidic channel 511 to define a detection zone within the microfluidic channel 511. The detection zone is a discrete volume of the microfluidic channel which will be subject to optical probing by a light source and light detector. In FIG. 5, the microfluidic channel 511 is orthogonal to the plane of the paper.

Alternatively, the optical element may form part of the channel or may be constructed as a single entity combined with the channel such as by injection moulding, for example.

In operation, a light source 512 emits diverging light into the input port 520 of the optical element 500. This light enters the element and reflects off the surface 517 of the optical element 500 into the adjoining light guide portion 515. The light may be guided down the light guide portion 515, by for example at least one internal reflection, to the output port 510 as shown by the light rays depicted in FIG. 5. The light may travel down the light channel 515 by total internal reflection.

Optionally, the surface 517 may be shaped or coated with a reflective coating to increase the amount of light directed into the light guide portion 515. The surface 517 is specifically shaped to reflect diverging light from the light source 512 such as an inorganic or organic LED. In embodiments, the surface 517 may be mirrored. The skilled person will understand that various shaping or coating techniques may be used to increase the amount of light from the source 512 which is directed into the light guide portion 515.

As can be readily understood from FIG. 5, light is guided from the light guide portion 515 to the detection zone within the microfluidic channel 511. In this embodiment, one face of the detection zone is illuminated with light from the light source 512.

The incident light entering the channel may interact with optically active material within the channel to cause the emission of light at a wavelength different to the wavelength of the incident light—for example, by a process such a fluorescence or phosphorescence—this process is depicted by element 530 in FIG. 5. This emitted light may be detected by the light detector 513 via a detection port 540 to indicate the presence of the optically active material within the detection zone. The light detector 513 may provide a quantitative or qualitative measurement. In other embodiments, the detection port 540 forms part of the optical element 500 itself. In such other embodiments, the portion of the channel coupled to the detection port 540 may also therefore form part of the optical element 500 itself. In embodiments, the optical element is integral with the channel.

In a further embodiment, the inner surface of at least a portion of the channel forming the detection zone is arranged to support a reagent on its surface.

The optically active material may be used to indicate the concentration of an analyte within the detection zone. The optically active material may be, for example, a fluorescent label which directly or indirectly binds to the analyte. The optically active material may be indirectly bound to the analyte via an antibody, for example. The skilled person will understand that a variety of techniques can be used to measure the concentration of an analyte using, for example, a fluorophore label. The device in accordance with embodiments will detect changes in the fluorescent signal, for example, within the detection zone to directly or indirectly indicate the presence of the analyte. By calibration and/or using a reference device in accordance with the present disclosure, the concentration of an analyte may inferred or calculated from the optical signal detected in the detection zone.

A device according to embodiments can therefore be used to perform assays to allow detection of an analyte within a fluid sample. Detection techniques are applicable to methods of specific-binding assays for quantitatively or qualitatively assaying analytes. For the avoidance of doubt, "analyte" refers to the species under assay and "specific binding partner" refers to a species to which the analyte will bind specifically.

Examples of analytes and specific binding partners which may be used are given below. In each case, either of the pair may be regarded as the analyte with the other as the specific binding partner: antigen and antibody; hormone and hormone receptor; polynucleotide strand and complementary polynucleotide strand; avidin and biotin; protein A and immunoglobulin; enzyme and enzyme cofactor (substrate); lectin and specific carbohydrate.

Embodiments may relate to a form of immunoassay known as a 2-site immunometric assay. In such assays, the analyte is "sandwiched" between two antibodies, one of which is labelled, directly or indirectly, with an entity that can be measured, e.g by optical or electrochemical means (detection antibody), and the other is immobilised, directly or indirectly, on a solid support (capture antibody).

The skilled person will understand that the present disclosure is equally applicable to analyses other than in vitro diagnostics, for example environmental, veterinary and food analysis.

It can also be understood that the present disclosure is equally applicable to heterogeneous, homogeneous immunoassays, fluorescent dye binding assays and other assay formats.

The device in accordance with the present disclosure provides a simple and low cost configuration for improved optical probing of a channel such as a microfluidic channel. In particular, it can be understood that the optical element 500 defines a detection zone and optical detection port 540, and permits the light source 512 and light detector 513 to be mounted side-by-side on one side of the device for performing an assay without the risk of source light swamping the detected signal.

The skilled person will understand that the wavelength of the light source and the working range of the detector are chosen to match the optically active material, such as a fluorophore. In other words, the light source and detector are tailored or matched to the optically active material. In essence, source light at a first wavelength is incident upon the fluid in the channel and an optical process such as fluorescence or phosphorescence occurs, if the optically active material is present, which results in the emission of light of a second wavelength which the detector can detect to indicate the presence of the optically active material, and therefore analyte as explained above.

Figure 6:
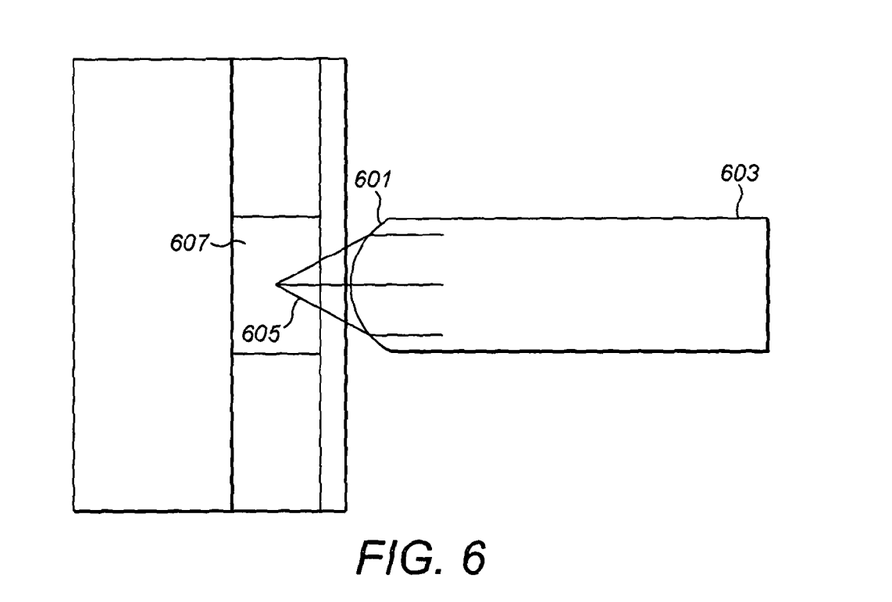

Optionally, the output port of the light guide portion 515 may be shaped to maximise the exiting light intensity at the detection zone, as shown in FIG. 6. The spherical shape of the output port 601 of the light guide portion 603 may focus light 605 into the detection zone 607.

A channel may be optically probed several times along its length by, for example, pairs of source/detectors arranged to detect one or more different analytes. The example shown in FIGS. 3 and 4 shows four optical elements. One of the source/detector pairs may be arranged for background light measurements.

In embodiments, the light source is an organic light emitting diode, based on either a small molecule or a polymer, and the light detector is a broadband photodetector based on organic semiconductors. In a typical system of this kind the light source would have a spectral width of 100 nm at half maximum and the photodetector would detect light from 400-650 nm.

However, it will be appreciated that any appropriate component or material can be adopted. For example, the LED may be an organic LED or an inorganic LED with a peak emission at c.500 nm, such as product Osram LVE63C-ABDA-35 from RS Components, or inorganic LED with a peak emission at 470 nm, such as product Kingbright KPTD-3216QBC-C from RS Components.

Any light detector may be suitable, such as an organic light detector based on an active layer formed from a 50:50 blend of 1-(3-Methoxycarbonylpropyl)-1-phenyl-[6.6]C61 (commonly known as PCBM) and poly(3-hexylthiophene) (commonly known as P3HT). However, it will be appreciated that any appropriate component or material can be adopted. For example, the detector may alternatively be an inorganic, silicon based photodiode such as Osram SFH2430 from RS Components. The skilled person will understand that the term detector includes qualitative and quantitative detection or measurement of radiation of a characteristic wavelength or wavelength range.

In an embodiment, there is provided a microfluidic device having at least one microfluidic channel having at least one dimension of less than 5 mm, optionally less than 1 mm. It will be appreciated that other dimensions of the channel and device may exceed this value.

Figure 7:
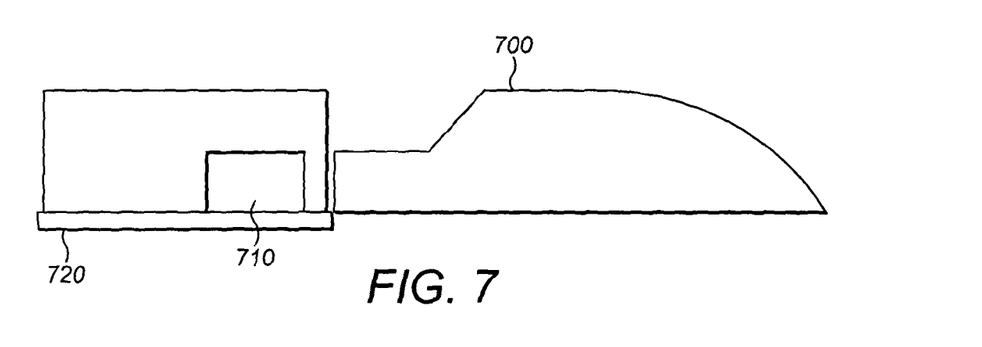
FIG. 7 shows a configuration in accordance with further embodiments.
Figure 8A:
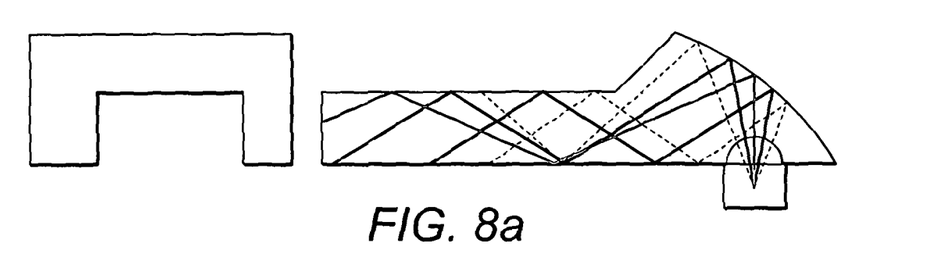
FIGS. 8a, 8b, 8c and 8d show alternative optical inputs for the device in accordance with embodiments of the present invention.
Figure 8B:
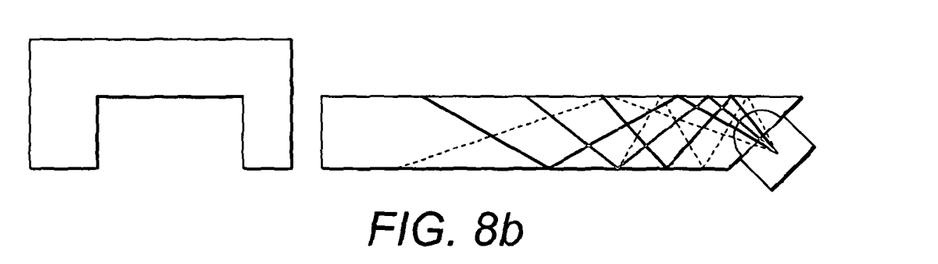
Figure 8C:
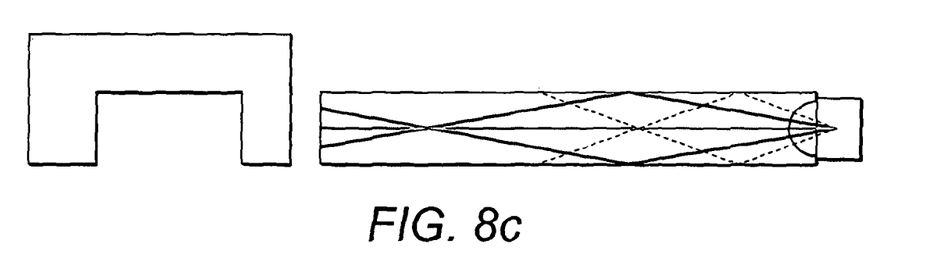
Figure 8D:
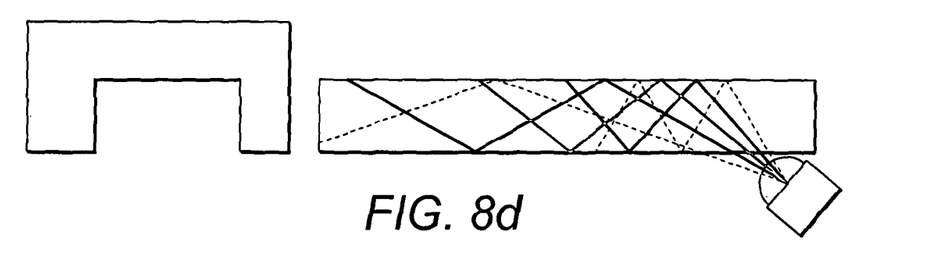

There is further provided an improved method for constructing a device for performing an assay. In particular, an improved method for mounting the source and detector in the improved geometry. Referring to FIG. 7, there is shown the optical element 700 comprising a detection zone 710 and sealing tape 720. As can be understood from the figures, the optical element is arranged to engage with a channel to define a detection zone. In embodiments, the optical element abuts the microfluidic channel and can be sealed with sealing tape 720. For example, the sealing tape 720 could be optically clear film coated with pressure sensitive adhesive, or an optically clear thermoplastic sealed by laser welding or ultrasonic welding. This configuration allows the light source and light detector to be mounted side-by-side on the same face of the substrate. Accordingly, a low cost and simple method for constructing a device for performing an assay is provided.

In other embodiments, the device for performing an assay and optical element/s may be integrally formed by, for example, injection moulding. The microfluidic chip including the optical element/s may be monolithic. It can be understood that the microfluidic chip and/or optical elements may be manufactured from any optically clear thermoplastic material, such as polystyrene, polycarbonate, polyester, polymethyl methacrylate or a cyclic polyolefin such as TOPAS, optionally doped with dye to act as an optical filter. The optical filter may be a short pass filter, for example, or a long pass filter.

FIG. 8 shows alternative configurations for the optical input of the optical element. As shown in FIG. 8*a*, the optical element may be arranged such that the light source at least partially embeds the optical device. Alternatively, the optical element may be arranged such that the light source embeds the optical element at an angled edge (FIG. 8*b*) or from an edge substantially perpendicular to the light channel (FIG. 8*c*). Further alternatively, the light source may be aligned at an angle to an optical axis of the light channel (FIG. 8*d*).

The skilled person will understand that all references to optical and light are made by way of example only and the present disclosure extends to cover other parts of the electromagnetic spectrum. For example, the device in accordance with the present invention is equally suitable for infrared probing using an infrared source and/or infrared detector.

Embodiments of the invention have been described by way of example only. It will be appreciated that variations of the described embodiments may be made which are still within the scope of the invention.

The invention claimed is:

1. A device for performing an assay comprising:
   a substrate comprising a channel;
   at least one optical element, each of the at least one optical elements comprising:
      an input port having an optical axis substantially perpendicular to the substrate;
      an output port optically coupled to at least a portion of the channel, the output port having an optical axis substantially parallel to the substrate; and
      a light guide portion optically connecting the input port and the output port, the light guide portion being configured to transmit incident light inputted at the input port in a direction along the optical axis of the input port to the output port such that the incident light is outputted from the output port and illuminates said least a portion of the channel in a direction along the optical axis of the output port; and
   for each of the at least one optical elements, a detection port spatially offset from the input port of the optical element associated with the detection port and optically coupled to said at least a portion of the channel, the detection port being configured to receive light emitted from the channel along an optical axis substantially parallel to the optical axis of the input port of the optical element associated with the detection port.

2. A device as claimed in claim 1 wherein the device for performing an assay is a microfluidic device and/or the channel is a microfluidic channel.

3. A device as claimed in claim 1 wherein each of the at least one optical elements further comprises a first surface arranged to receive light from the input port and direct said light into the light guide portion.

4. A device as claimed in claim 3 wherein in each of the at least one optical elements the first surface is convexly shaped or reflectively coated.

5. A device as claimed in claim 1 wherein the device further comprises an input fluid reservoir and an output fluid reservoir, and the channel connects the input fluid reservoir to the output fluid reservoir.

6. A device as claimed in claim 1 wherein the output port of each of the at least one optical elements is arranged to abut said at least a portion of the channel.

7. A device as claimed in claim 1 wherein the device is monolithic.

8. A device as claimed in claim 1 wherein each of the at least one optical elements is formed of material incorporating a dye to provide optical filtering.

9. A device as claimed in claim 1 wherein said at least a portion of the channel further comprises at least one of beads, baffles, scaffold, rod or tubing arranged to support a reagent.

10. A device as claimed in claim 9 further comprising, for each of the at least one optical elements, a light source optically coupled to the input port and/or a light detector optically coupled to the detection port.

11. A device as claimed in claim 10 wherein the light source and the light detector are both present, and wherein the light source and the light detector are mounted on the same side of the substrate.

12. A device as claimed in claim 10 wherein the light source and light detector are mounted on a common subassembly.

13. A device as claimed in claim 9, wherein the reagent is an antibody.

14. A device as claimed in claim 1 wherein an inner surface of said at least a portion of the channel is arranged to support a reagent.

15. A device as claimed in claim 1 wherein in each of the at least one optical elements the output port has a convexly curved surface.

16. A device as claimed in claim 1, wherein the device further includes a light source, the input port of each of the at least one optical elements being optically coupled to the light source.

17. A method of fabricating a microfluidic device for performing assay, the microfluidic device comprising a substrate having a microfluidic channel, the method comprising:
coupling at least one optical element to the channel, each of the at least one optical elements comprising
an input port having an optical axis substantially perpendicular to the substrate,
an output port optically coupled to at least a portion of the microfluidic channel, the output port having an optical axis substantially parallel to the substrate, and
a light guide portion optically connecting the input port and output port, the light guide portion being configured to transmit incident light inputted at the input port in a direction along the optical axis of the input port to the output port such that the incident light is outputted from the output port and illuminates said least a portion of the channel in a direction along the optical axis of the output port;
coupling a light source to the input port of each of the at least one optical elements, and
for each of the at least one optical elements, coupling a light detector to a detection port wherein the detection port is optically coupled to the microfluidic channel, is spatially offset from the input port of the optical element associated with the detection port, and has an optical axis substantially parallel to the optical axis of the input port of the optical element associated with the detection port, the detection port being configured to receive light emitted from the channel along an optical axis substantially parallel to the optical axis of the input port of the optical element associated with the detection port, and the light source and light detector are mounted on the same side of the microfluidic device.

18. A method for performing an assay, the method comprising:
providing a device comprising
a substrate comprising a channel;
an optical element comprising:
an input port;
an output port optically coupled to at least a portion of the channel; and
a light guide portion optically connecting the input port and output port; and
a detection port spatially offset from the input port of the optical element and optically coupled to said at least a portion of the channel;
inputting incident light from a light source to the input port of the optical element along an optical axis substantially perpendicular to the substrate;
guiding the incident light from the light source through the light guide portion of the optical element and to the output port of the optical element;
transmitting the incident light from the output port of the optical element to the channel along an optical axis substantially parallel to the substrate; and
transmitting emitted light from the channel to the detection port along an optical axis substantially parallel to the optical axis along which the incident light is inputted to the input port of the optical element.

* * * * *